(12) United States Patent
Arii et al.

(10) Patent No.: US 7,140,231 B2
(45) Date of Patent: Nov. 28, 2006

(54) EVOLVED GAS ANALYZING METHOD AND APPARATUS

(75) Inventors: Tadashi Arii, Tokyo (JP); Yoshihiro Takata, Tokyo (JP)

(73) Assignee: Rigaku Corporation, Akishima (JP)

( * ) Notice: Subject to any disclaimer, the term of this patent is extended or adjusted under 35 U.S.C. 154(b) by 94 days.

(21) Appl. No.: 10/919,477

(22) Filed: Aug. 17, 2004

(65) Prior Publication Data

US 2005/0112027 A1 May 26, 2005

(30) Foreign Application Priority Data

Aug. 18, 2003 (JP) ............... 2003-294758
Feb. 3, 2004 (JP) ............... 2004-026473

(51) Int. Cl.
*G01N 30/72* (2006.01)
(52) U.S. Cl. ............... 73/23.37; 73/23.22; 73/23.35; 73/23.36; 250/339.07; 250/339.13
(58) Field of Classification Search ............... 73/19.01, 73/19.02, 23.2, 23.22, 23.34, 23.35, 23.37; 250/339.07, 339.13
See application file for complete search history.

(56) References Cited

U.S. PATENT DOCUMENTS

| | | | | |
|---|---|---|---|---|
| 4,525,328 A | * | 6/1985 | Bredeweg | ............... 422/80 |
| 5,442,175 A | * | 8/1995 | Dawson | ............... 250/288 |
| 5,528,032 A | * | 6/1996 | Uchiyama | ............... 250/288 |
| 5,588,746 A | * | 12/1996 | Minobe et al. | ............... 374/10 |
| 6,053,059 A | * | 4/2000 | Muranaka et al. | ............... 73/863.12 |
| 6,125,687 A | * | 10/2000 | McClelland et al. | ............... 73/19.01 |

FOREIGN PATENT DOCUMENTS

| | | |
|---|---|---|
| FR | 2 734 363 | 11/1996 |
| GB | 1 582 304 | 1/1981 |
| JP | 11-83802 | 3/1999 |
| JP | 11-281620 | 10/1999 |
| JP | 2001-91438 | 4/2001 |
| JP | 2002-174606 | 6/2002 |

OTHER PUBLICATIONS

S. Daveau et al., "Electrical conduction phenomena in coked industrial reforming catalysts" Materials Research Bulletin, vol. 32, No. 2, 1997, pp. 205-212.

\* cited by examiner

*Primary Examiner*—Hezron Williams
*Assistant Examiner*—David A. Rogers
(74) *Attorney, Agent, or Firm*—Westerman, Hattori, Daniels & Adrian, LLP (57) ABSTRACT

An evolved gas analysis system contains a first measurement step of heating a first sample containing measurement target material and non-measurement target material at a predetermined temperature programming rate and detecting the amount of gas evolved from the first sample; a second measurement step of heating a second sample achieved by excluding the measurement target material from the first sample at the same temperature increasing rate as the first measurement step, and detecting the amount of gas evolved from the second sample; and a correcting step of calculating the amount of gas evolved from the measurement target material on the basis of the detected data of the respective steps.

6 Claims, 12 Drawing Sheets

MEASUREMENT START CONDITION

START TEMPERATURE  50.0  °C ▷

START DEGREE OF VACUUM  3.0  $10^{-6}$ Pa ▷

MEASUREMENT CONDITION

| | SET TEMPERATURE | UNIT | TEMPERATURE PROGRAMMING RATE | UNIT | HOLDING TIME | UNIT | RECORD-ING | EXECUTION FREQUENCY | RETURN |
|---|---|---|---|---|---|---|---|---|---|
| 1 | 1200.0 | °C ▷ | 30 | K/min ▷ | 0 | min ▷ | ☑ | | ☐ |
| 2 | | ▷ | | ▷ | | ▷ | ☐ | | ☐ |
| 3 | | ▷ | | ▷ | | ▷ | ☐ | | ☐ |
| 4 | | ▷ | | ▷ | | ▷ | ☐ | | ☐ |
| 5 | | ▷ | | ▷ | | ▷ | ☐ | | ☐ |
| 6 | | ▷ | | ▷ | | ▷ | ☐ | | ☐ |
| 7 | | | | | | | | | ☐ |

EVOLVED GAS ANALYZING METHOD AND APPARATUS

FIELD OF THE INVENTION

The present invention relates to evolved gas analyzing method and apparatus represented by a temperature programmed desorption analyzing method or the like.

DESCRIPTION OF THE RELATED ART

The temperature programmed desorption analyzing method is a thermal analyzing method for measuring the amount of evolved gas desorbed from a solid sample as a function of sample temperature when the temperature of the sample is increased at a controlled rate, and it is also called as TDS (Thermal Desorption Spectroscopy) or TPD (Temperature Programmed Desorption).

The temperature programmed desorption analyzing method is implemented by a temperature programmed desorption analyzing apparatus equipped with a sample chamber for disposing a sample, a heating furnace for heating the sample in the sample chamber, a mass spectrometer serving as detecting means for detecting gas desorbed from the sample, and a turbo molecular pump (TMP) for forming a measuring environment of a high vacuum atmosphere (see JP-A-2002-174606, for example).

According to general-purpose thermal analysis such as thermogravimetry (TG), differential thermal analysis (DTA), differential scanning calorimetry (DSC) or the like, in order to enhance data precision, measurement of a standard sample is carried out separately from measurement of a sample being measured. Background data caused by a measurement environment is detected from the measurement data of the standard sample, and the background data is subtracted from the measurement data of the sample to be measured, thereby determining the original measurement data.

In an evolved gas analyzing method, for example, a gas chromatography/mass spectrometer (GC/MS), a method of subtracting any mass spectrum from peak data (peak mass spectrum) to delete background has been used. However, a method of subtracting background data from measurement data under the same temperature along a temperature function has not been used.

Recently, a semiconductor wafer obtained by forming thin film on a silicon substrate has been targeted as a measurement object of the evolved gas analyzing method, and analysis of thin film (measurement target materials) by using the evolved gas analyzing method has been broadly carried out. In the evolved gas analyzing method, desorbed gas is generated from the material contained in semiconductor wafer, and the desorbed gas from the thin film can be relatively easily detected because the peak of the evolved gas amount varies depending on the temperature.

In the vicinity of the temperature at which the desorbed gas is evolved from the thin film as the measurement target material, another desorbed gas may be evolved from contaminant adhering to a silicon substrate. It has been hitherto general that the desorbed gas evolved from such contaminant can be neglected because the amount thereof is remarkably minute as compared with the amount of the desorbed gas evolved from the thin film. However, it has been recently required to carry out the evolved gas analysis more precisely, and in order to satisfy this requirement, it has been needed to detect only the desorbed gas evolved from the measurement target material (thin film).

SUMMARY OF THE INVENTION

In view of the foregoing situation, the inventors of this application have been studied and accomplished high-precision analysis on measurement target materials. Therefore, an object of the present invention is to provide an evolved gas analyzing method which can be carried out highly precise analysis of the measurement target materials, and an evolved gas analyzing apparatus which can perform the evolved gas analyzing method efficiently.

In order to attain the above object, according to a first aspect of the present invention, there is provided an evolved gas analyzing method comprising:

a first measurement step of disposing a first sample in a sample chamber, heating the first sample at a predetermined temperature programming rate and detecting the amount of gas evolved from the first sample in a measurement chamber intercommunicating with the sample chamber; and a second measurement step of disposing a second sample in the sample chamber, heating the second sample at the same temperature programming rate as the first measurement step, and detecting the amount of gas evolved from the second sample in the measurement chamber intercommunicating with the sample chamber, wherein the evolved gas amounts of the first and second samples are compared with each other on the basis of detected data of the first and second measurement steps.

By comparing the detected data obtained in the first and second measurement steps, application fields of the evolved gas analysis can be expanded.

In the evolved gas analyzing method described above, the first measurement step is carried out for the first sample which contains a measurement target material and a non-measurement target material, and the second measurement step is carried out for the second sample which contains a sample achieved by excluding the measurement target material from the first sample. A correcting step of calculating the amount of gas evolved from the measurement target material is further included.

That is, the evolved gas analyzing method of the present invention is applicable to various kinds of samples each containing a measurement target material and a non-measurement target material which can be measured while being separated from the measurement target material. For example, one of these kinds of samples may be a semiconductor wafer obtained by forming the thin film (measurement target material) on the surface of a silicon substrate. In the case of a semiconductor wafer, the second measurement step is carried out on the silicon substrate as the second sample. Subsequently, the first measurement step is carried out on the semiconductor wafer containing the silicon substrate and the thin film formed on the surface of the silicon substrate as the first sample.

Here, it is important to carry out each of the measurement steps substantially at the same temperature programming rate. A desorption reaction follows a reaction rate because it is based on a chemical reaction. In general, the desorption temperature is shifted to a higher temperature side as the temperature programming rate is increased. Accordingly, if the temperature programming rate of each measurement step is different, it would be impossible to carry out the correcting step along a temperature function.

Furthermore, it is important that the respective measurement steps are carried out under the same measurement conditions. For example, in the temperature-programmed desorbed gas analysis using a mass spectrometer, a mass sweeping range (range of m/z) of the mass spectrometer, a filament applying current for ionization, an applied voltage of an ion detector (secondary electron multiplier), a detection integrated time of ion current, etc. are set to be identical for the respective measurement steps.

In the correcting step, the detected data achieved in the respective measurement steps with respect to the same temperature are subjected to operation processing to calculate the amount of gas evolved from the measurement target material. The amount of gas evolved from each sample is varied depending on the temperature. Accordingly, by conducting the operation processing on the amounts of gases evolved from the respective samples at the same temperature, the amounts of gases desorbed from measurement target material along a temperature function can be determined with high precision.

In a case where the present invention is applied to a temperature-programmed desorbed gas analysis which is carried out while a sample is disposed under a vacuum atmosphere, when the sample temperature at the measurement start time and the degree of vacuum in the measurement chamber are different between the respective measurement steps, the difference in measurement condition affects the comparison result, and thus it may be difficult to grasp a minute difference in desorbed gas amount. Furthermore, when the sample temperature at the measurement start time and the degree of vacuum in the measurement chamber are greatly different between the respective measurement steps, the comparison between the evolved gas amounts of the respective samples achieved in the respective measurement steps is originally difficult.

Therefore, when the evolved gas analyzing method of the present invention is carried out under the vacuum atmosphere, it is preferable that the temperature of a sample disposed in the sample chamber and the degree of vacuum in the measurement chamber are monitored and each measurement step is started at the time when the sample disposed in the sample chamber is heated until the temperature of the sample is increased to a predetermined temperature and the degree of vacuum in the measurement chamber is equal to a predetermined degree of vacuum.

Furthermore, it is also preferable that the temperature of the sample disposed in the sample chamber is heated to the predetermined temperature and kept at the predetermined temperature, and each measurement step is started at the time when the degree of vacuum in the measurement chamber is set to the predetermined degree of vacuum.

By matching the measurement condition (the sample temperature and the degree of vacuum in the measurement chamber) at the measurement start time between the measurement steps as described above, the evolved gas amounts of the respective samples achieved in the respective measurement steps can be compared with each other with high precision.

According to a second aspect of the present invention, there is provided an evolved gas analyzing apparatus comprising: a sample chamber for disposing a sample, a heating furnace for heating the sample in the sample chamber, a sample temperature measuring unit for measuring the temperature of the sample, a heating furnace controller for controlling the temperature of the heating furnace on the basis of detected data of the sample temperature measuring unit; a measurement chamber intercommunicating with the sample chamber, a desorbed gas detecting unit for detecting gas desorbed from the sample in the measurement chamber; a desorbed gas detecting controller for controlling the desorbed gas detecting unit; and a data processing unit for analyzing the detected data of the desorbed gas detecting unit in association with the sample temperature. The heating furnace controller executes a first measurement step of heating a first sample disposed in the sample chamber and a second measurement step of heating a second sample disposed in the sample chamber at the same temperature programming rate, and the data processing unit compares the evolved gas amounts of the respective samples on the basis of the detected data of the desorbed gas detecting unit in the respective measurement steps.

Here, it is preferable that on the basis of the detected data of the desorbed gas detecting unit in the first measurement step carried out for the sample containing a measurement target material and a non-measurement target material as the first sample, and the detected data of the desorbed gas detecting unit in the second measurement step carried out for the sample achieved by excluding the measurement target material from the first sample as the second sample, the data processing unit calculates the amount of gas evolved from the measurement target material.

Furthermore, it is preferable that the detected data achieved in the respective measurement steps with respect to the same temperature are subjected to operation processing, and the amount of gas evolved from the measurement target material is calculated.

The evolved gas analyzing apparatus of the present invention may be equipped with a vacuum pumping unit for vacuum-pumping the measurement chamber, and a degree of vacuum measuring unit for measuring the degree of vacuum in the measurement chamber, wherein the desorbed gas detecting controller starts recording of a detected data output from the desorbed gas detecting unit when the sample disposed in the sample chamber is heated until the temperature thereof is increased to a predetermined temperature and also the degree of vacuum in the measurement chamber is equal to a predetermined degree of vacuum.

Furthermore, the heating furnace controller heats the sample disposed in the sample chamber such that the temperature thereof is equal to a predetermined temperature and the sample is kept at the predetermined temperature, and also heats the sample disposed in the sample chamber at a predetermined temperature programming rate when the predetermined degree of vacuum is set in the measurement chamber.

According to the apparatus of the present invention, the evolved gas analyzing method of the present invention described above can be performed efficiently.

According to the present invention, the measurement data (background data) concerning the gas desorbed from the non-measurement target material are removed from the measurement data (overall data) concerning the gas desorbed from the sample containing the measurement target material and the non-measurement target material, so that only the amount of the gas desorbed from the measurement target material can be detected and thus the measurement target material can be analyzed with high precision.

DETAILED DESCRIPTION OF THE PREFERRED EMBODIMENTS

Preferred embodiments according to the present invention will be described with reference to the accompanying drawings.

Figure 1:
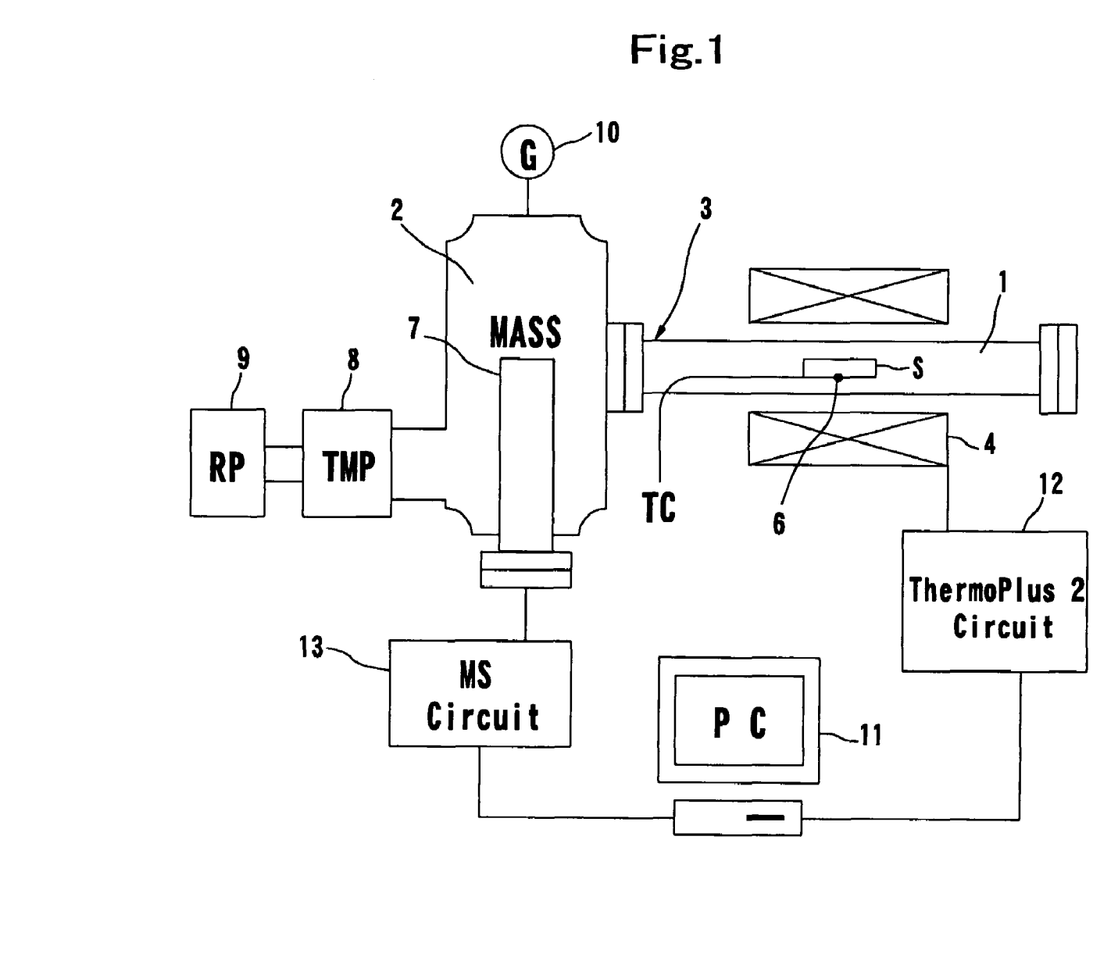
FIG. 1 is a diagram showing a temperature programmed desorption analyzing apparatus as an evolved gas analyzing apparatus according to an embodiment of the present invention.

A temperature programmed desorption analyzing apparatus has a main body 3 equipped with a sample chamber 1 and a measurement chamber 2 which intercommunicate with each other. An infrared heating furnace 4 serving as a heating unit is mounted around the sample chamber 1 so that a sample S disposed in the sample chamber 1 can be uniformly heated by the infrared heating furnace 4 surrounding the sample S. The sample S is disposed in the hollow portion of the sample chamber 1 while held by a sample holder. A thermocouple 6 serving as a sample temperature measuring unit is mounted on the sample holder to measure the temperature of the sample S.

A mass spectrometer 7 serving as a desorbed gas detecting unit is equipped in the measurement chamber 2. Gas desorbed from the sample S by heating is passed from the sample chamber 1 to the measurement chamber 2, and the mass spectrometer 7 ionizes and captures the desorbed gas to detect the desorbed gas.

A turbo molecular pump 8 serving as a vacuum pumping unit and a vacuum pump 9 (for example, a rotary pump or dry pump) for roughing vacuum pumping are linked to the measurement chamber 2. The turbo molecular pump 8 exhausts undesired gas remaining in the hermetically-closed space extending from the sample chamber 1 to the measurement chamber 2 by vacuum-pumping, and also guides gas desorbed from the sample S in the sample chamber 1 to the measurement chamber 2.

Furthermore, a vacuum gauge 10 serving as a degree of vacuum measuring unit is mounted in juxtaposition with the measurement chamber 2. The degree of vacuum in the measurement chamber 2 is monitored by the vacuum gauge 10 at all times. An ion gauge may be used as the vacuum gauge 10, for example.

The infrared heating furnace 4 is controlled by a control circuit (heating furnace control circuit) 12, and the mass spectrometer 7 is controlled by a control circuit (MS control circuit) 13. These control circuits 12 and 13 are connected to a personal computer 11 functioning as a central processing device, and control the infrared heating furnace 4 and the mass spectrometer 7 on the basis of instruction signals from the personal computer 11, respectively. That is, the heating furnace control circuit 12 and the personal computer 11 function as a heating furnace control unit for controlling the temperature of the infrared heating furnace 4, and the MS control circuit 13 and the personal computer 11 function as a desorbed gas detection control unit for controlling the mass spectrometer 7.

Figure 2:
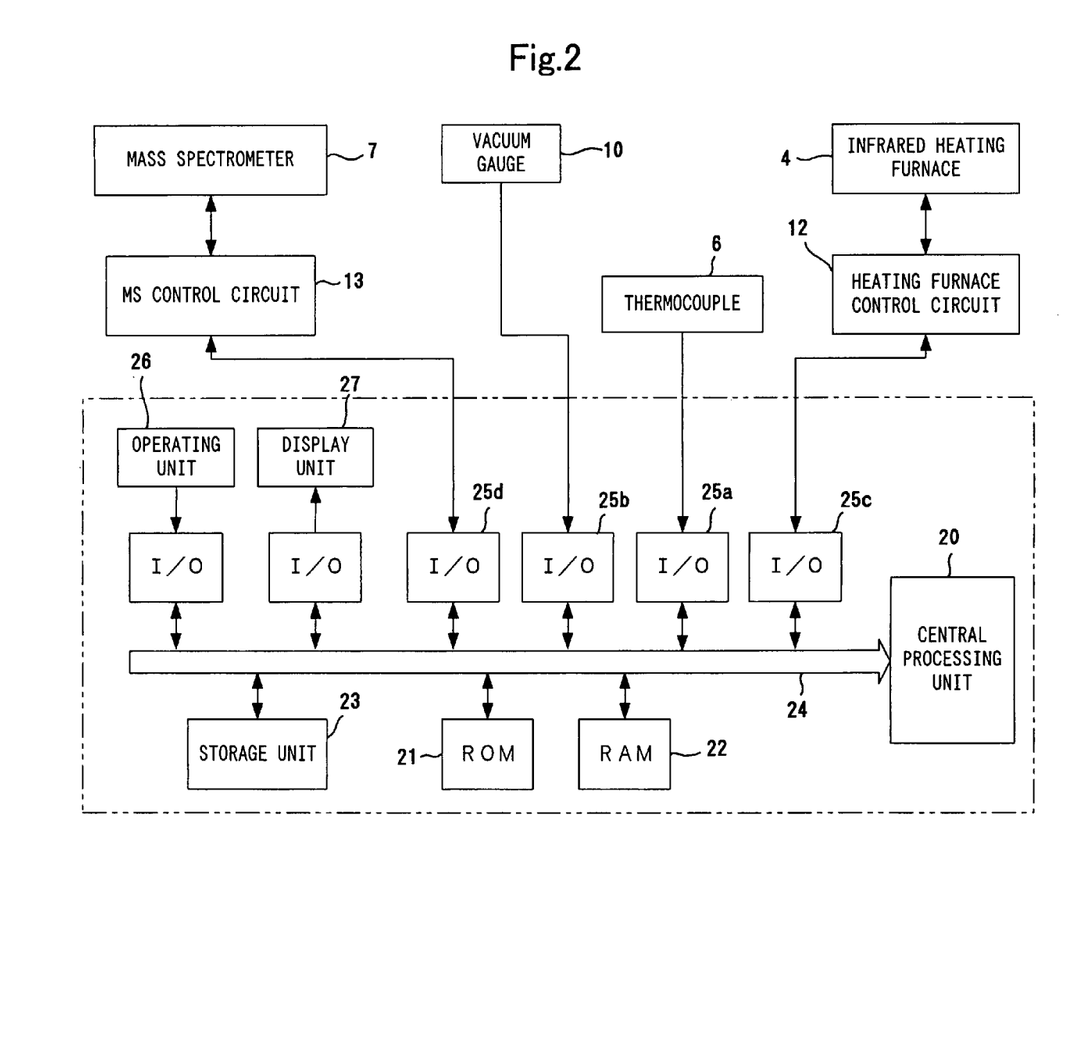
FIG. 2 is a block diagram showing a control system for an infrared heating furnace and a mass spectrometer.

FIG. 2 is a block diagram showing the control system for the infrared heating furnace and the mass spectrometer.

As well known, the personal computer 11 is equipped with a central processing unit (CPU) 20, ROM 21 (Read Only Memory), RAM 22 (Random Access Memory) and a storage unit 23 (for example, hard disk), which are designed to perform mutual data communications with one another through a bus 24. The thermocouple 6, the vacuum gauge 10, the heating furnace control circuit 12 and the MS control circuit 13 are connected to the personal computer 11 through input/output interfaces 25a, 25b, 25c, 25d. The personal computer 11 is equipped with an operating unit 26 such as a keyboard, a mouse, etc., a display unit 27 such as a liquid crystal display or the like, etc.

When the personal computer 11 is powered on, the central processing unit 20 reads out and executes a starting program stored in ROM 2, and also starts an operating system (OS) stored in the storage unit 23.

An evolved gas analysis program is stored in the storage unit 23 in advance. The central processing unit 20 executes the control of the infrared heating furnace 4 and the mass spectrometer 7 on the basis of the evolved gas analysis program, and also analyzes detected data transmitted from the mass spectrometer 7 in association with the sample temperature. AS described above, the personal computer 11 also functions as a data processing unit.

The personal computer 11 is supplied with temperature measurement data of the sample S from the thermocouple 6, and also supplied with measurement data concerning the degree of vacuum in the measurement chamber 2 (degree of vacuum measurement data) from the vacuum gauge 10.

Figure 3:
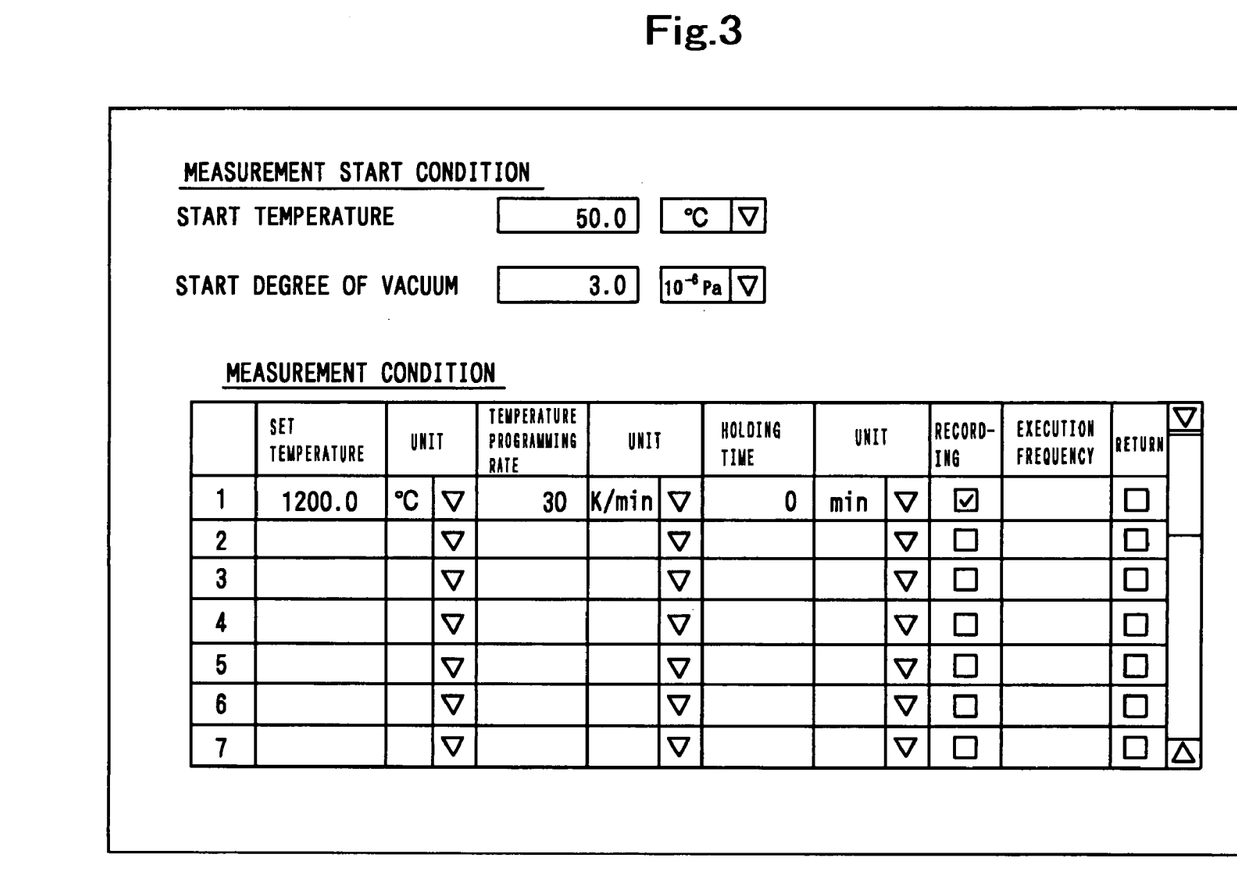
FIG. 3 is a diagram showing a set screen of an evolved gas analyzing program.

The evolved gas analysis program stored in the personal computer 11 has a function of displaying a set screen (display frame) as shown in FIG. 3, which enables an operator to set a measurement start condition and a measurement condition on the set screen.

The measurement start condition contains a sample temperature at the measurement start time (measurement start temperature) and a degree of vacuum in the measurement chamber 2 (measurement start degree of vacuum). The central processing unit 20 outputs an instruction signal for starting the measurement to the heating furnace control circuit 12 and the MS control circuit 13 at the time when the sample is heated until the temperature thereof is equal to a predetermined measurement start temperature and also the degree of vacuum in the measurement chamber 2 reaches a predetermined measurement start degree of vacuum.

Here, it is very rare that both the sample temperature and the degree of vacuum in the measurement chamber 2 reach the corresponding predetermined measurement start conditions at the same time, and it is general that the sample temperature reaches the predetermined measurement start condition before the degree of vacuum in the measurement chamber 2 reaches the measurement start degree of vacuum. Therefore, the evolved gas analysis program outputs to the heating furnace control circuit 12 an instruction signal which instructs to keep the sample temperature to the measurement start temperature until the degree of vacuum in the measurement chamber 2 reaches the predetermined measurement start degree of vacuum.

As the measurement condition such as the set temperature of the sample, the temperature programming rate until the set temperature concerned, the holding time at the set temperature, recording or non-recording, etc. may be arbitrarily set. The central processing unit 20 outputs the instruction signals for starting the measurement to the heating furnace control circuit 12 and the MS control circuit 13 on the basis of the measurement condition thus set. The heating furnace control circuit 12 controls the infrared heating furnace 4 on the basis of the instruction signal concerned to heat the sample S at a predetermined temperature programming rate until the temperature of the sample S is equal to the set temperature. At the same time, the MS control circuit 13 controls the mass spectrometer 7 according to the instruction signal. The mass spectrometer 7 detects gas desorbed from the sample S, and outputs the detected data through the MS control circuit 13 to the personal computer 11. In the personal computer 11, the measurement result of the desorbed gas thus input thereto is temporarily stored in the storage unit 23.

The central processing unit 20 analyzes the measurement result of the desorbed gas stored in the storage unit 23 in association with the sample temperature. Various analyzing modes are preset in the evolved gas analysis program, and one of them is an analyzing mode of comparing the detected data of the desorbed gas achieved from the first and second samples and calculating the amount of the evolved gas of the measurement target material contained in the first sample according to the flowchart of an evolved gas analyzing method described later.

Next, an embodiment of the evolved gas analyzing method of the present invention will be described.

This embodiment will be described on the assumption that the thin film formed on a semiconductor wafer is a measurement target material. In this embodiment, the semiconductor wafer has a thin film formed on the surface of a silicon substrate, and the silicon wafer is set as a first sample. That is, the first sample contains not only the thin film as a measurement target material, but also non-measurement target materials such as the silicon substrate and contaminants adhering to the silicon substrate.

Here, the silicon substrate before the thin film is formed thereon is set as a second sample. The second sample excludes the thin film as the measurement target material, and contains only the non-measurement target material such as the silicon substrate and the contaminants adhering to the silicon substrate.

Figure 4:
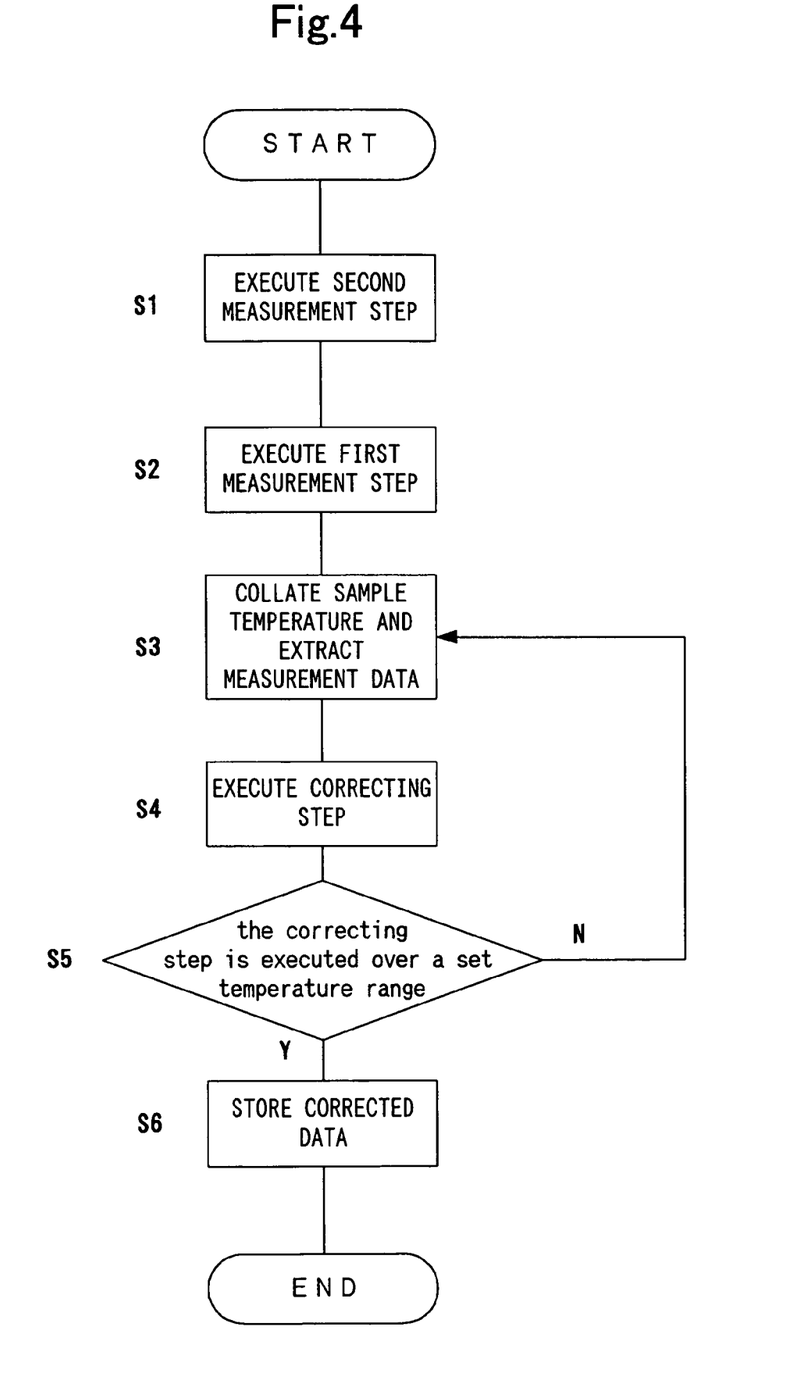
FIG. 4 is a flowchart showing a processing step of the evolved gas analyzing method according to the embodiment.

FIG. 4 is a flowchart showing the processing steps of the evolved gas analyzing method according to this embodiment.

[Second Measurement Step]

First, the second sample (hereinafter referred to as "sample S") is put in a sample holder and disposed in the hollow portion of the sample chamber 1, and then the second measurement step is carried out (step S1).

In the second measurement step, the central processing unit 20 of the personal computer 11 monitors temperature measurement data transmitted from the thermocouple 6. When the central processing unit 20 judges that the temperature of the sample S reaches a predetermined measurement start temperature, the central processing unit 20 outputs an instruction signal to the heating furnace control circuit 12 so as to keep the temperature of the sample to the measurement start temperature. According to this instruction signal, the heating furnace control circuit 12 controls the infrared heating furnace 4 to keep the temperature of the sample S in the sample chamber 1 to the measurement start temperature.

Furthermore, the central processing unit 20 monitors degree of vacuum measurement data transmitted from the vacuum gauge 10. When the central processing unit 20 judges that the degree of vacuum in the measurement chamber 2 reaches a predetermined measurement start degree of vacuum, with this judgment as a trigger, the central processing unit 20 outputs instruction signals for starting the measurement (second measurement step) to the heating furnace control circuit 121 and the MS control circuit 13.

On the basis of the instruction signal, the heating furnace control circuit 12 controls the infrared heating furnace 4. Under this control, the sample S is heated to a set temperature at a predetermined temperature programming rate. At the same time, the MS control circuit 13 controls the mass spectrometer 7. The mass spectrometer 7 detects desorbed gas from the sample S, and outputs the amount of detection gas through the MS control circuit 13 to the personal computer 11. In the personal computer 11, the measurement result of the desorbed gas thus input is temporarily stored in the storage unit 23.

Figure 5:
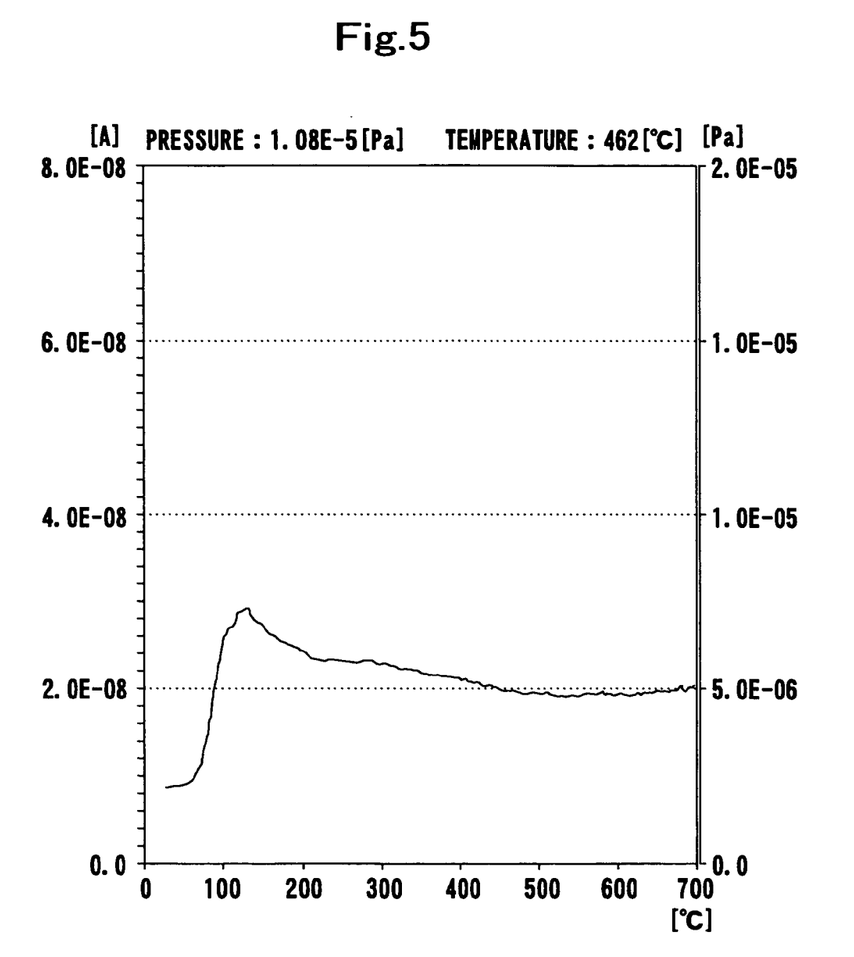
FIG. 5 is a diagram showing an example of detected data achieved by a second measurement step.

FIG. 5 is a graph showing the detected data achieved in the second measurement step. In FIG. 5, the abscissa axis represents the sample temperature, and the ordinate axis represents the amount of gas evolved from the second sample (ion relative intensity). The detected data shows variation of the evolution amount of gas desorbed from the non-measurement target material such as the silicon substrate and the contaminants adhering to the silicon substrate in the second sample with a temperature function.

[First Measurement Step]

Next, the first sample (hereinafter referred to as "sample S") is put in the sample holder and disposed in the hollow portion of the sample chamber 1, and the first measurement step is carried out under the same measurement start condition and the same measurement condition as the second measurement step (step S2 of FIG. 4).

According to the first measurement step, as in the case of the second measurement step, the central processing unit 20 of the personal computer 11 also monitors temperature measurement data transmitted from the thermocouple 6, and when the sample temperature reaches a predetermined measurement start temperature, the central processing unit 20 outputs an instruction signal to the heating furnace control circuit 12 so as to keep the measurement start temperature. The heating furnace control circuit 12 controls the infrared heating furnace 4 according to the instruction signal to keeps the temperature of the sample S in the sample chamber 1 to the measurement start temperature.

Furthermore, the central processing unit 20 monitors the degree of vacuum measurement data transmitted from the vacuum gauge 10, and when the central processing unit 20 judges that the degree of vacuum in the measurement chamber 2 reaches a predetermined measurement start degree of vacuum, with this judgment as a trigger, the central processing unit 20 outputs an instruction signal for starting the first measurement step to the heating furnace control circuit 12 and the MS control circuit 13.

On the basis of this instruction signal, the heating furnace control circuit 12 controls the infrared heating furnace 4. Under this control, the sample S is heated to a set temperature at a predetermined temperature programming rate. At the same time, the MS control circuit 13 controls the mass spectrometer 7. The mass spectrometer 7 detects gas desorbed from the sample S, and outputs the detected data through the MS control circuit 13 to the personal computer 11. In the personal computer 11, the measurement result of the desorbed gas thus input is stored in the storage unit 23.

It is preferable that the first and second measurement steps are executed while the other measurement conditions in the respective measurement steps, such as a mass sweeping range (range of m/z) of the mass spectrometer, filament applied current for ionization, an applied voltage of an ion detector (secondary electron multiplier), a detection integrated time of ion current, etc. are set to be identical between the respective measurement steps.

Figure 6:
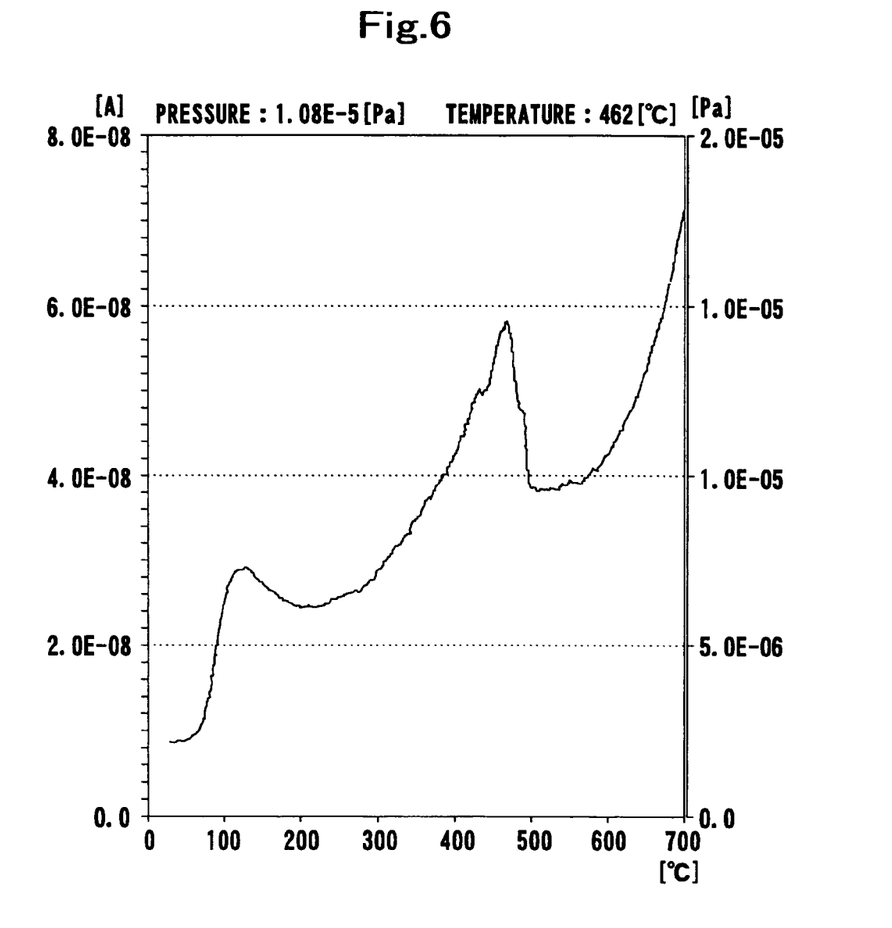
FIG. 6 is a diagram showing an example of detected data achieved by a first measurement step.

FIG. 6 is a graph showing the detected data obtained in the first measurement step. In FIG. 6, the abscissa axis represents the sample temperature, and the ordinate axis represents the evolved gas amount (ion relative intensity) from the sample as in the case of FIG. 5. These detected data contain the evolution amount of the gas desorbed from the thin film (measurement target material) constituting the semiconductor wafer serving as the first sample, and also the evolution amount of the gas desorbed from the non-measurement target material such as the silicon substrate and the contaminants adhering to the silicon substrate, and FIG. 6 shows the total evolution amount of these desorbed gases represented by a temperature function.

[Correcting Step]

Subsequently, the sample temperature is collated, the evolved gas amounts at the same sample temperature in the respective measurement steps are determined, and the correcting step is executed (steps S3, S4, S5 of FIG. 4). That is, the central processing unit 20 of the personal computer 11 reads out the detected data in the measurement steps stored in the storage unit 23, and compares the detected data thus read out to calculate the evolved gas amount of the measurement target material contained in the sample 1.

The mass spectrometer 7 cannot continuously detect the evolved gas amount because of its property. That is, the mass spectrometer 7 captures and detects desorbed gas from the continuously-heated sample at any time interval. Accordingly, no detected data may exist at some sample temperature in each measurement step. Therefore, as shown in FIGS. 5 and 6, the detected data obtained by the mass spectrometer 7 may be linearly supplemented (interpolated) in a desired temperature range to calculate continuous detected data as a function containing the sample temperature as a variable, whereby the evolved gas amount at the same sample temperature in each measurement step can be determined.

In this case, the detected data of the desired temperature range are subjected to linear interpolation (supplement) to determine the continuous detected data represented by a function containing the sample temperature as a variable, however, in place of the linear interpolation, function approximation, spline approximation or the like may be used.

In the correcting step, the central processing unit 20 calculates the evolved gas amounts at the same sample temperature in the respective measurement steps, and subtracts from the detected data of the first measurement the desorbed gas evolution amount of the non-measurement target material such as the silicon substrate and the contaminants adhering to the silicon substrate (that is, the detected data of the second measurement step). Accordingly, only the evolution amount of the gas desorbed from the thin film (measurement target material) can be calculated.

Figure 7:
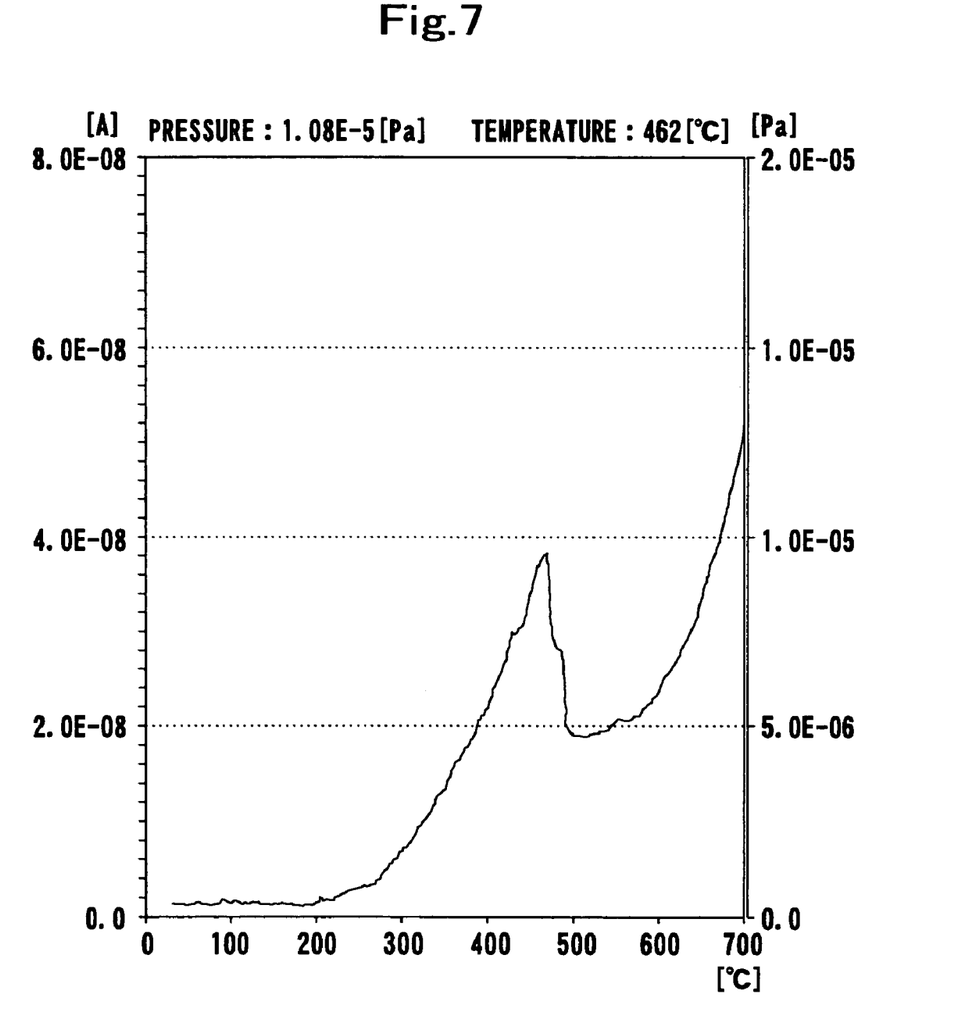
FIG. 7 is a diagram showing an example of detected data achieved by a correcting step.

FIG. 7 is a graph showing the detected data achieved in the correcting step.

After the correcting step is executed over a set temperature range (step S5), the data after correction are stored and the evolved gas analysis is finished.

The present invention is not limited to the above embodiments, and various modifications may be made to the above embodiment.

For example, the present invention may be applied to evolved gas analysis other than the temperature programmed desorption analyzing method. Furthermore, in the above embodiment, the measurement start degree of vacuum is preset as the measurement start condition in the evolved gas analysis program stored in the personal computer 11, and the central processing unit 20 monitors the degree of vacuum measurement data from the vacuum gauge 10. However, the present invention is not limited to this mode. For example, the above embodiment may be modified so that the vacuum gauge 10 is equipped with a measurement start degree of vacuum setting function, the vacuum gauge 10 directly monitors the degree of vacuum in the measurement chamber 2, and the vacuum gauge 10 outputs a detection signal to the central processing unit 20 when the degree of vacuum in the measurement chamber 2 reaches the measurement start degree of vacuum. In this case, the central processing unit 20 outputs an instruction signal for starting the measurement with the above detection signal as a trigger.

EXAMPLE

Figure 8:
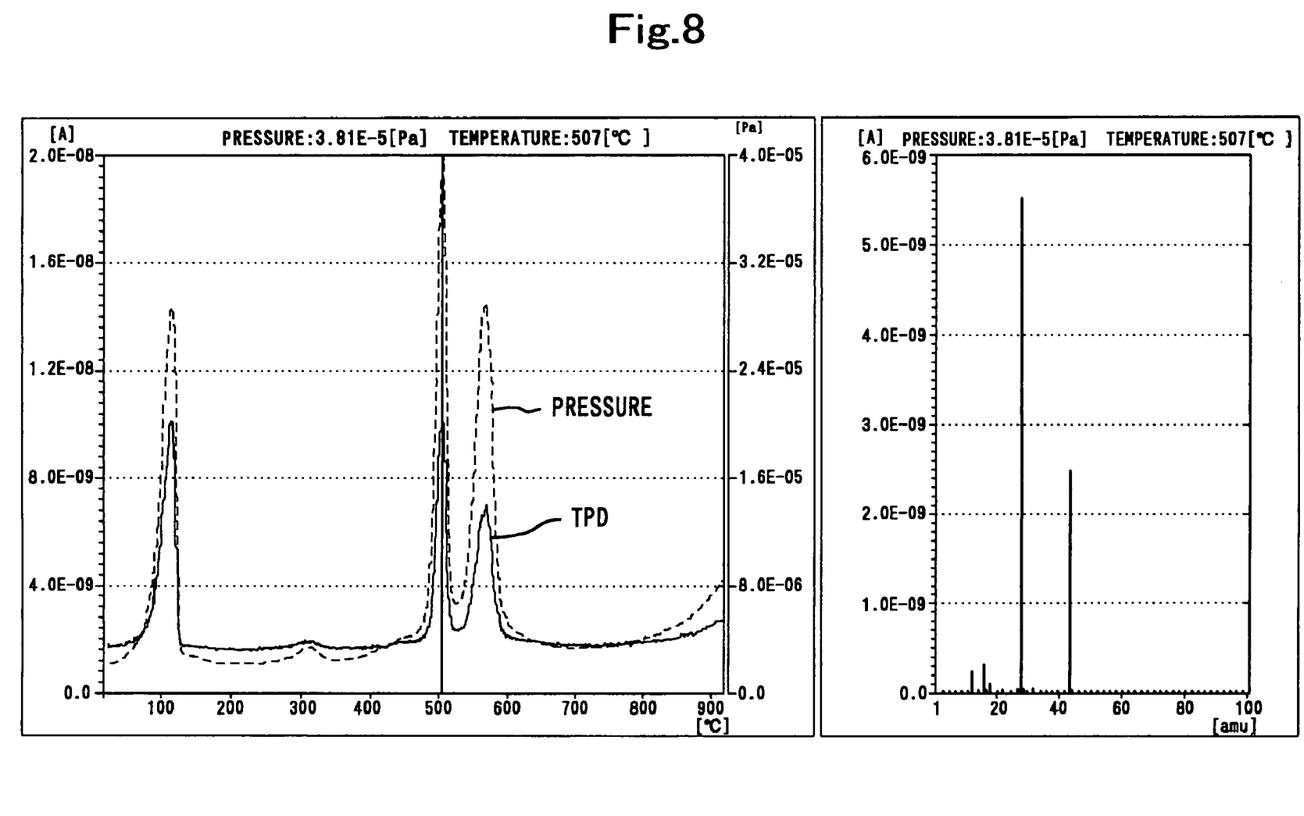
FIG. 8 is a diagram showing a measurement result achieved when calcium oxalate monohydrate material (measurement target material) is disposed in a platinum cell (non-measurement target material) and temperature programmed desorbed gas analysis (second measurement step) is carried out.
Figure 9:
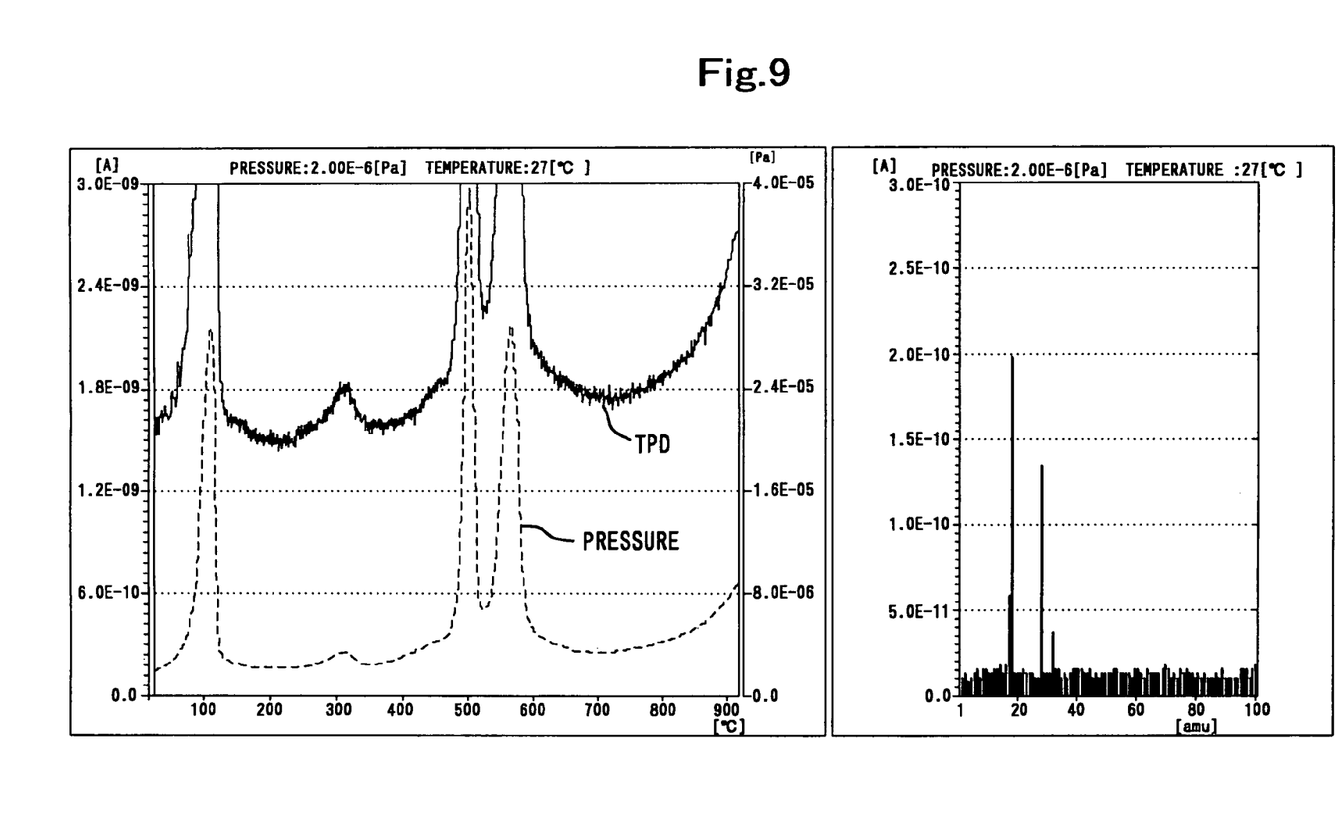
FIG. 9 is an enlarged view of a measurement start portion of FIG. 8.

Calcium oxalate monohydrate material (measurement target material) of 76.5 µg was disposed in a platinum cell (non-measurement target material), and the temperature programmed desorbed gas analysis was executed (second measurement step). FIG. 8 shows a measurement result thus achieved, and shows the relationship between the ion intensity (TPD) of desorbed gas detected by the mass spectrometer at each measurement temperature and the degree of vacuum. FIG. 9 is an enlarged view of a measurement start portion of FIG. 8.

Figure 10:
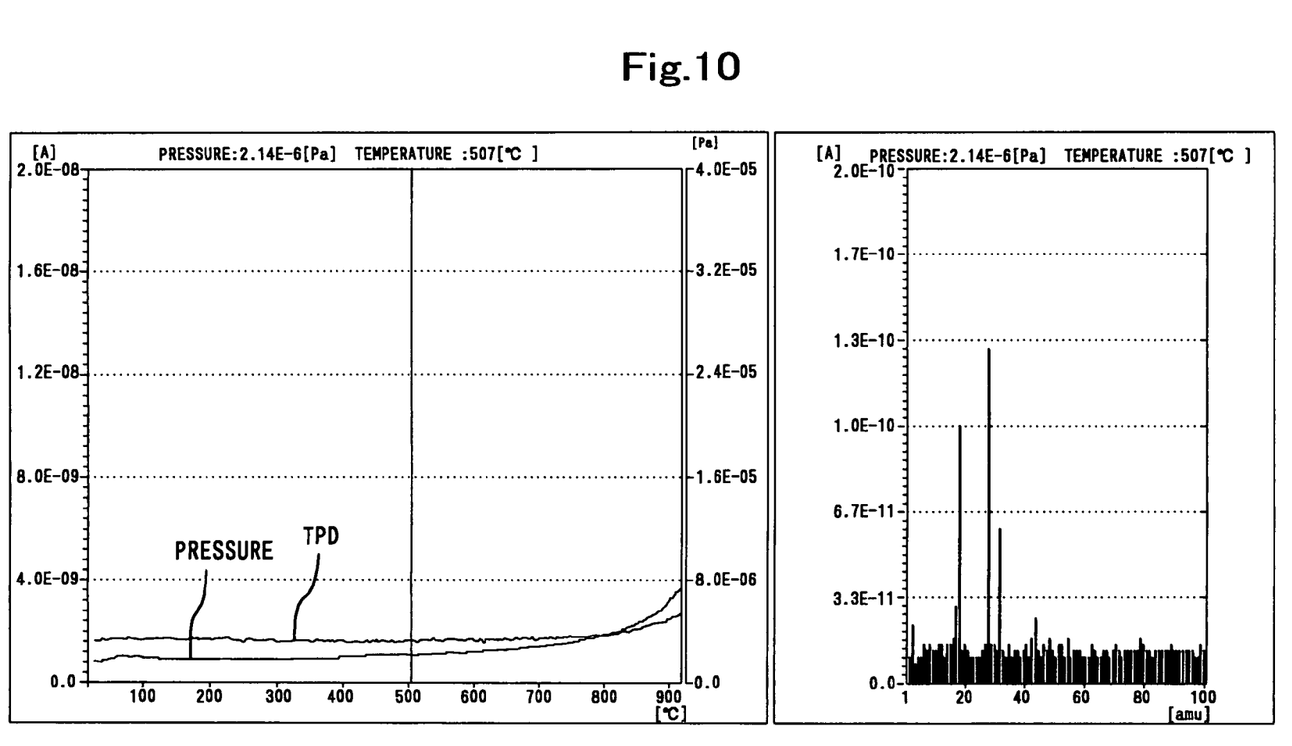
FIG. 10 is a diagrams showing a measurement result when only the platinum cell (non-measurement target material) is heated and the temperature programmed desorbed gas analysis (first measurement step) is carried out.

Subsequently, only the platinum cell (non-measurement target material) was heated at the same temperature programming rate as the preceding measurement (second measurement), and the temperature programmed desorbed gas analysis was executed. FIG. 10 shows a measurement result thus achieved, and shows the relationship between the ion intensity (TDP) of the desorbed gas detected by the mass spectrometer at each measurement temperature and the degree of vacuum. FIG. 10 is an enlarged view of the measurement start portion of FIG. 11.

Figure 11:
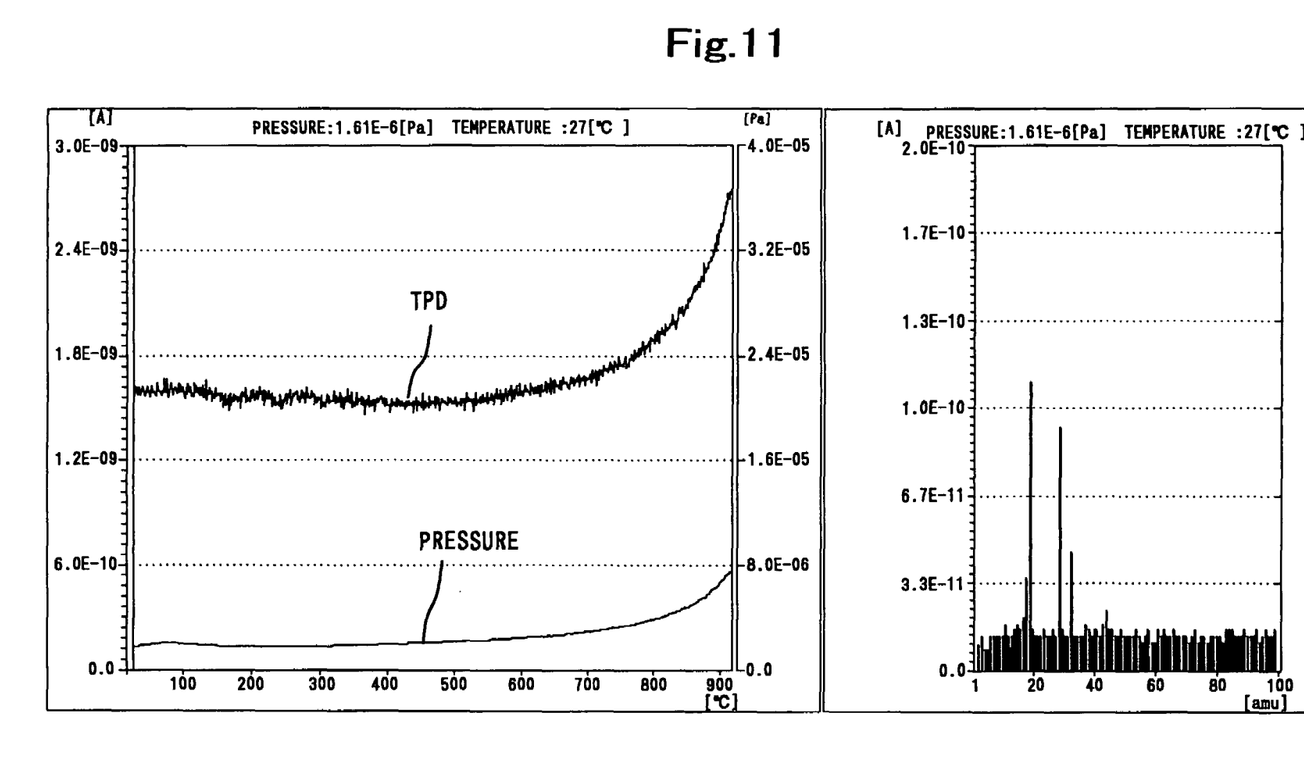
FIG. 11 is an enlarged view of a measurement start portion of FIG. 10.

Here, as shown in FIGS. 9 and 11, when the degree of vacuum and the temperature at the measurement start time (the left end of the graph) were set to be substantially identical between the respective measurement steps, the ion intensity (TPD) data of the desorbed gas exhibited substantially the same value in the respective measurement steps.

Figure 12:
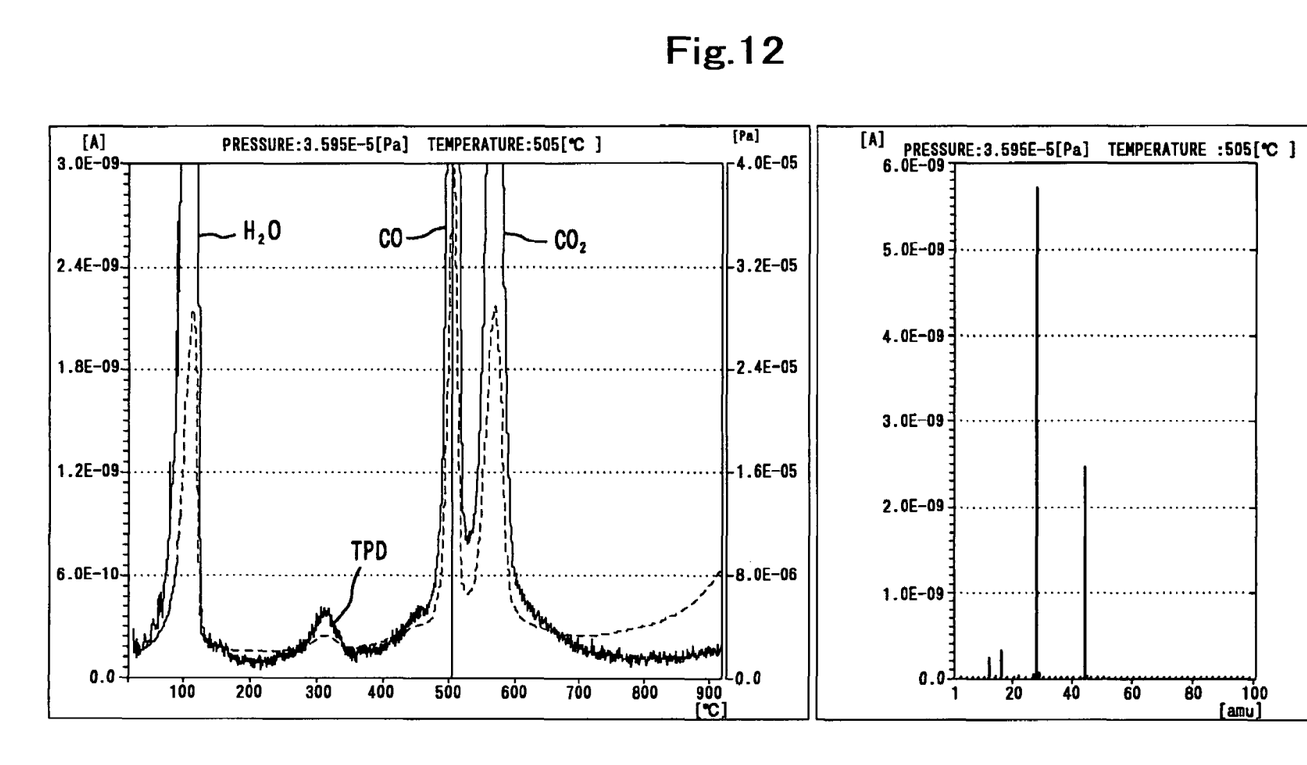
FIG. 12 is a diagram showing a result achieved when correction processing is conducted on a measurement result achieved in the second measurement step by using TPD data of only the platinum cell as a blank on the basis of the measurement results of FIG. 8 and d10.

FIG. 12 is a result achieved by correcting the measurement result achieved in the second measurement step while TPD data based on only the platinum cell is set as a blank.

By setting the degree of vacuum and the temperature at the measurement start time point substantially identical between the respective steps as described above, the measurement results of the respective measurement steps can be compared with each other under the same measurement condition, so that the ion intensity of gas desorbed from the measurement target material can be detected with high precision by properly removing the data associated with the blank (see FIG. 12).

In the above embodiments, the infrared heating furnace is used as the heating unit. However, the heating unit of the present invention is not limited to the infrared heating furnace, and various other well-known heating means such as an electric heater, a burner, a laser, etc. may be used. Furthermore, in the above embodiments, two measurement steps are carried out on two samples to remove the background data, that is, to accurately achieve the data of only the measurement target material. However, the number of measurement steps (and the number of samples) is not limited to two, and it may be three or more. That is, a plurality of measurement steps may be sequentially carried out in the same manner as the above embodiments to eliminate the effect of data of gas desorbed from non-measurement target materials and thus accurately detect respective data of a plurality of measurement target materials.

What is claimed is:

1. An evolved gas analyzing method comprising:
    carrying out a first measurement step, comprising:
        disposing a first sample having a measurement target material and a non-measurement target material in a sample chamber,
        heating the first sample to a predetermined temperature;
        maintaining the predetermined temperature;
        reducing the atmosphere inside the sample chamber to a predetermined pressure at the predetermined temperature;
        starting measurement of the amount of gas evolved from the first sample at the predetermined temperature and at the predetermined pressure, the amount of gas evolved being measured in a measurement chamber intercommunicating with the sample chamber; and
        raising the temperature at a predetermined temperature programmed rate while continuing the measurement of the amount of gas evolved from the first sample to obtain a first detected data set;
    carrying out a second measurement step, comprising:
        disposing a second sample of the non-measurement target material in the sample chamber;
        heating the second sample to the predetermined temperature;
        maintaining the predetermined temperature;
        reducing the atmosphere inside the sample chamber to the predetermined pressure at the predetermined temperature;
        starting measurement of the amount of gas evolved from the second sample at the predetermined temperature and at the predetermined pressure, the amount of gas evolved being measured in the measurement chamber intercommunicating with the sample chamber; and
        raising the temperature at the predetermined temperature programmed rate while continuing the measurement of the amount of gas evolved from the second sample to obtain a second detected data set; and
    comparing the first data set with the second data set.

2. The evolved gas analyzing method according to claim 1, wherein said evolved gas analyzing method further comprises a correcting step of calculating the amount of gas evolved from the measurement target material.

3. The evolved gas analyzing method according to claim 2, wherein in the correcting step, the amount of gas evolved from the measurement target material at a given temperature is calculated by subtracting the first detected data set at the given temperature from the second detected data set at the given temperature.

4. The evolved gas analyzing method according to claim 1, wherein the first and second measurement steps are carried out under the same measurement conditions.

5. An evolved gas analyzing apparatus comprising:
    a sample chamber for disposing a first sample and a second sample;
    a heating furnace for heating the first sample and the second sample disposed in the sample chamber;
    a sample temperature measuring unit for measuring the temperature of the first sample and the second sample;
    a heating furnace controller for controlling the temperature of the heating furnace on the basis of the temperature measured by the sample temperature measuring unit;
    a measurement chamber intercommunicating with the sample chamber;
    an evolved gas detecting unit for detecting the amount of gas evolved from the first sample and the second sample;
    an evolved gas detecting controller for controlling the evolved gas detecting unit;
    a data processing unit for analyzing the detected data of the evolved gas detecting unit in association with the sample temperature,
    a vacuum pumping unit for reducing the pressure inside the measurement chamber; and
    a vacuum measuring unit for measuring the pressure inside the measurement chamber,
    wherein the evolved gas analyzing apparatus is capable of carrying out:
        a first measurement step, comprising:
            heating the first sample of a measurement target material and a non-measurement target material to a predetermined temperature;
            maintaining the predetermined temperature;
            reducing the atmosphere inside the sample chamber to a predetermined pressure at the predetermined temperature;
            starting measurement of the amount of gas evolved from the first sample at the predetermined temperature and at the predetermined pressure, the amount of gas evolved being measured in a measurement chamber intercommunicating with the sample chamber; and
            raising the temperature at a predetermined temperature programmed rate while continuing the measurement of the amount of gas evolved from the first sample to obtain a first detected data set;
        carrying out a second measurement step, comprising:
            heating the second sample of the non-measurement target material at the temperature programming rate to the predetermined temperature;
            maintaining the predetermined temperature;
            reducing the atmosphere inside the sample chamber to the predetermined pressure at the predetermined temperature;
            starting measurement of the amount of gas evolved from the second sample at the predetermined temperature and at the predetermined pressure, the amount of gas evolved being measured in the measurement chamber intercommunicating with the sample chamber; and raising the temperature at the predetermined temperature programmed rate while continuing the measurement of the amount of gas evolved from the second sample to obtain a second detected data set; and a comparing step for comparing the first data set with the second data set.

6. The evolved gas analyzing apparatus according to claim 1, wherein the data processing unit calculates the evolved gas amount from the measurement target amount at a given temperature by subtracting the first detected data set at a given temperature from the second detected data set at the given temperature.

* * * * *